United States Patent [19]
Jayne et al.

[11] Patent Number: 6,040,574
[45] Date of Patent: Mar. 21, 2000

[54] ATMOSPHERIC-PARTICLE ANALYZER

[75] Inventors: John T. Jayne, Littleton; Douglas R. Worsnop, Lexington; Charles E. Kolb, Sudbury, all of Mass.

[73] Assignee: Aerodyne Research, Inc., Billerica, Mass.

[21] Appl. No.: 09/035,048

[22] Filed: Mar. 5, 1998

[51] Int. Cl.$^7$ .................................................. H01J 49/04
[52] U.S. Cl. ........................................ 250/288; 250/251
[58] Field of Search ................................. 250/288, 251, 250/294, 295

[56] References Cited

U.S. PATENT DOCUMENTS

| | | | |
|---|---|---|---|
| 3,679,973 | 7/1972 | Smith, Jr. et al. | 324/71 R |
| 3,808,433 | 4/1974 | Fite et al. | 250/251 |
| 3,854,321 | 12/1974 | Dahneke | 73/28 |
| 3,924,123 | 12/1975 | Schmidt | 250/251 |
| 4,383,171 | 5/1983 | Sinha et al. | 207/135 |
| 5,270,542 | 12/1993 | McMurry et al. | 250/288 |
| 5,382,794 | 1/1995 | Downey et al. | 250/288 |
| 5,426,301 | 6/1995 | Turner | 250/288 |
| 5,681,752 | 10/1997 | Prather | 250/288 |

*Primary Examiner*—Jack Berman
*Attorney, Agent, or Firm*—Cesari and McKenna

[57] ABSTRACT

The principle object of the invention is to provide an improved particle analyzer for analyzing particles contained in a gaseous medium. A more specific object is to provide a particle analyzer that provides a measure of the concentration of particles of various sizes in the atmosphere and the make up of the particles of various sizes. A more specific object is to provide an analyzer of the foregoing type which is small inexpensive and suitable for unattended use in the field.

7 Claims, 2 Drawing Sheets

ATMOSPHERIC-PARTICLE ANALYZER

BACKGROUND OF THE INVENTION

This invention relates to the analysis of atmospheric samples for particulate contaminants. More particularly it relates to an analyzer that determines both the size distribution and chemical make-up of atmospheric aerosol particles as a function of particle size.

Fine atmospheric aerosols have recently been indicted as a serious health threat. These particles can be generated in aircraft and automobile engines, coal and gas fired power plants, painting/depainting facilities, gas discharge boiler operations and in the atmosphere through chemical reactions of gaseous precursors. In addition to being a direct health threat, atmospheric aerosols also influence the climate by scattering and/or absorbing sunlight and by altering cloud coverage, which impacts both absorption and scattering of solar radiation. Full particulate emission/ambient concentration characterization requires determining both particle size distributions and chemical content, which often varies with particle size. At present this is a time-consuming and expensive task because available commercial instrumentation can size airborne aerosol particle distributions; however, measurement of the chemical contents of aerosol particles is performed in a separate stage, using laboratory procedures. No commercial instrument is available to automatically size the particles and simultaneously determine the composition as a function of their size in real time.

The need for sophisticated instrumentation for on-line, real-time aerosol composition analysis is widely acknowledged and various groups have been engaged in developing new technology for this purpose. The prior approaches of which we are aware involved the coupling of high-power lasers to induce aerosol ablation/vaporization and ionization, followed by time of flight (TOF) or quadrupole mass spectrometric analysis. Typically a light-scattering signal caused by a particle passing through a visible laser light beam is used to detect the spatial presence of a particle and to initiate a timing sequence for the firing of the vaporization laser. Reliable and efficient coupling of the complex laser triggering circuits with high-power pulsed laser and high-vacuum mass spectrometry technology, however, is a formidable task, especially under difficult field measurement conditions.

SUMMARY OF THE INVENTION

The aerosol analyzer described herein is based on novel variations of standard mass spectrometer technology, coupled with newly developed sizing technologies. The atmospheric gases entraining the particles to be analyzed are introduced into a sampling inlet, aerodynamically focused into a particle beam and then separated according to particle size. Particles of a succession of sizes are then projected onto a heated filament where they are vaporized and ionized. The resulting fractions are passed through a mass spectrometer for analysis of the various gaseous constituents. Since the particles whose constituents are processed by the spectrometer generally arrive at the heated filament singly, the spectrometer output can also be used to count the particles and therefore provide a measure of the particle concentration, the distribution of the various particle sizes, and the chemical compositions thereof.

More specifically, the atmospheric gases entering the system are passed through a beam forming unit of the type described in U.S. Pat. No. 5,270,542. In one embodiment of the invention, the beam is then passed through a charging system which saturates the particles with an electric charge, for example, by means of a flood of electrons, as is also described in U.S. Pat. No. 5,270,547. The charge on each particle is a function of the diameter of the particle such that the charge-to-mass ratio is a function of the particle size.

The charged beam then passes through an electric field between a pair of plates and is thereby deflected off axis, the degree of deflection depending on the particle size. An off-axis slit in a wall positioned downstream from the deflection plates thus passes a narrow range of particle sizes corresponding to the deflection imparted by the electric field. These particles are vaporized, counted and analyzed as described above. By varying the voltage between the deflection plates, one can pass a succession of particle sizes through the slit and thereby obtain a distribution of particle sizes as well as the constituents of the particles of various sizes.

In an alternative particle separation arrangement, we make use of the fact that the particles emerging from the beam-forming unit have different velocities, i.e., the velocity decreases with particle increasing size. The particle beam exiting from the beam-forming unit is periodically interrupted so as to provide a pulsed particle stream. As each pulse travels toward the detector it spreads along the direction of travel, so that the particles arrive at the detector in succession in accordance with particle size. The detector output as a function of time, during the arrival of each pulse, thus provides an indication of particle size distribution, as well as the compositions of particles of various sizes.

BRIEF DESCRIPTION OF THE DRAWINGS

The invention description below refers to the accompanying drawings, of which.

DETAILED DESCRIPTION OF AN ILLUSTRATIVE EMBODIMENT

Figure 1:
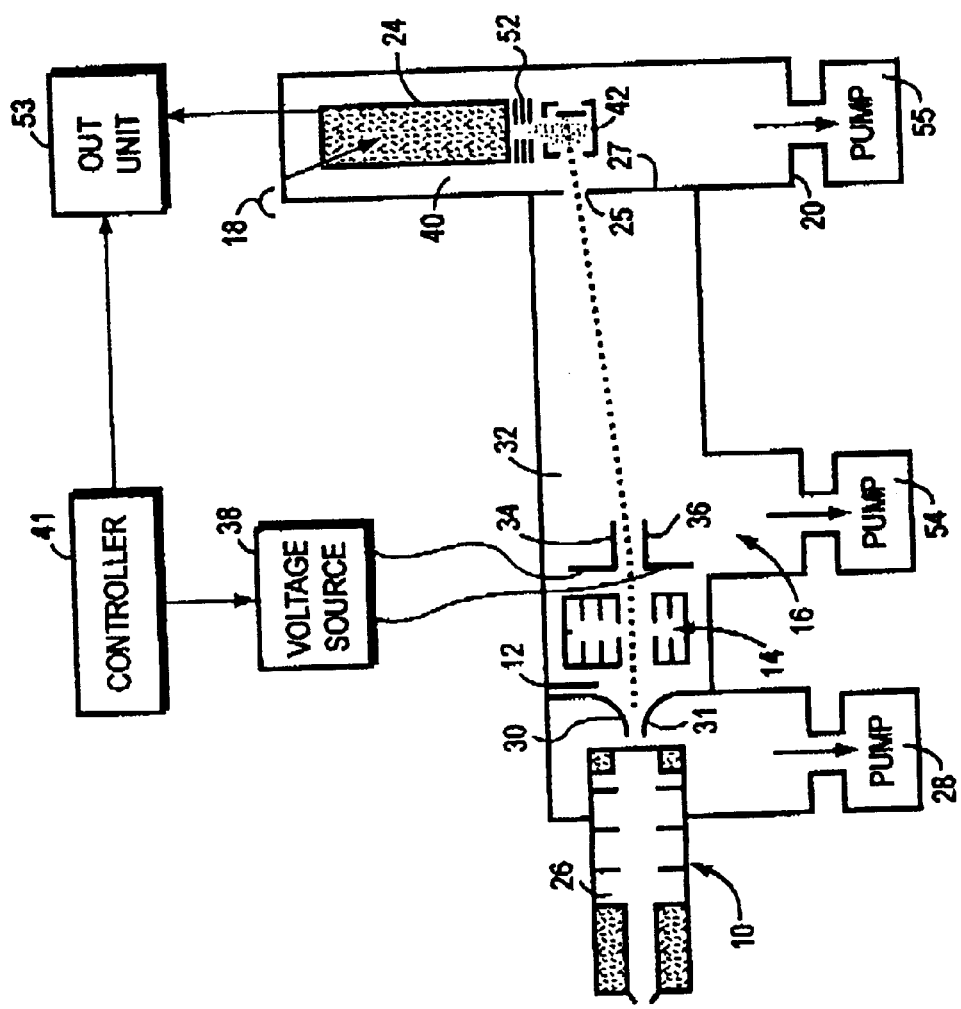
FIG. 1 is a diagram of a particle analyzer incorporating the invention.

As shown in FIG. 1, an analyzer incorporating the invention comprises a beam former 10 which draws in atmospheric gases entraining particles to be analyzed and forms a beam of these particles as indicated at 12. The beam passes through a particle charging unit 14 that applies an electric charge to the particles and then it passes through a deflection section 16 where an electric field deflects the beam as indicated in the drawing. A portion of the deflected beam passes through a selector 18 to a detector 20. In the detector 20 the particles are analyzed and counted by means of a molecular mass spectrometer 24 following vaporization and ionization. The system is operated under reduced pressure using turbomolecular pumps 28, 54 and 55. In the embodiment of the invention depicted in FIG. 1, the selector 18 comprises an off-axis slit 25 in a wall 27.

The beam former 10 is of the type described in the aforementioned U.S. Pat. No. 5,270,542. It includes a beam focuser 26, constructed to provide both the prefocusing and primary focusing functions described in the latter patent. The focused beam 12 passes through an aperture 30 to a chamber 32 containing the charge unit 14 and the deflection unit 16.

The aperture 30 is preferably at the end of a tapered projection 31 that protrudes into the supersonic gas expansion region at the exit of the beam-focuser 26 and provides efficient separation of the particles from the expanding gas. The projection may have a linear taper (conical) or, preferably, a hyperbolic taper as illustrated in FIG. 1. The use of a hyperbolic skimmer minimizes gas-particle collisions and thereby preserves the particle-size-dependent velocities which are generated by the beam focuser 26.

The charge unit preferably comprises an electron gun that floods the beam 12 with electrons and thus saturates the beam particles with an electric charge. The deflection unit 16 comprises a pair of parallel deflection plates 34 and 36 connected to a variable voltage source 38.

In passing through the field between the plates 34 and 36, each of the particles is deflected, the degree of deflection of each particle depending on its charge-to-mass ratio, its velocity and the voltage between plates 34 and 36. Accordingly, the particles in a relatively narrow range of particle size pass through the off-axis slit 25 into a chamber 40 containing the detector 20. The voltage of the source 38 is swept by a controller 41 over a range such that particles of a succession of sizes are passed to the detector 20.

Figure 2:
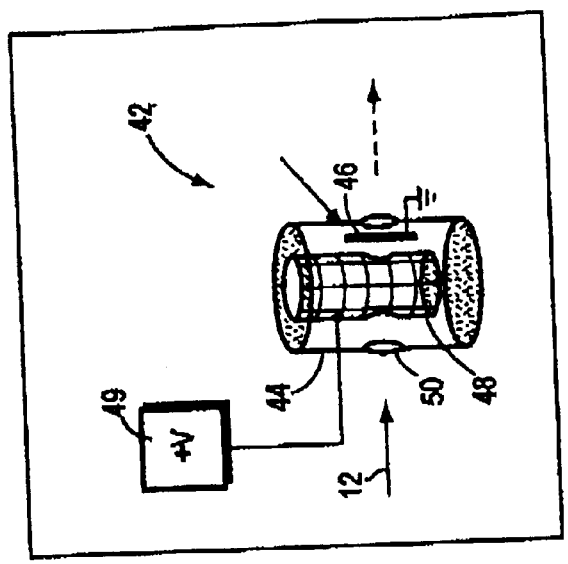
FIG. 2 is a detailed diagram of the particle vaporization unit used in the analyzer.

The detector 20 includes a particle vaporization and ionization unit 42 shown in detail in FIG. 2. It comprises a housing 44 containing a heated cathode 46 and a cylindrical electrical acceleration grid 48 which is connected to a positive voltage source 49. The particle beam enters the ionization unit through an aperture 50 in the housing 44, passes through the grid 48 and impinges on the cathode 46. The heated filament vaporizes the volatile and semi-volatile constituents of the particles and the resulting gaseous molecules expand into the interior of the grid 48.

The cathode 46 may be an electrical filament coated with an electron-emitting material such as thorium. The emitted electrons are accelerated toward and into the interior of the grid 48 by the electric field between the cathode 46 and the grid. Collisions of these electrons with the gaseous molecules enclosed by the grid dislodge electrons from the molecules, thereby positively ionizing them. The ions pass upward (FIG. 1) through an ion optics unit 52 to the mass spectrometer 24 for molecular analysis. Alternatively, electron emission and particle vaporization can be provided by separate filaments, powered independently to provide increased control over both functions.

The controller 41 also provides an output to an output unit 53, which displays or records the output of the mass spectrometer 24, thereby correlating the spectrometer output with the beam deflection voltage and thus with particle size.

In the ionization unit 42 electrons can also attach to molecules and molecular fragments with positive electron affinities. The resulting negatively charged ions can be detected by reversing the polarity of the ion optics or by mounting a second, negative ion, mass spectrometer opposite the positive ion mass spectrometer. Ionization can also be accomplished by flooding the region encompassed by the grid 48 with ionizing radiation from a suitable source.

Figure 3:
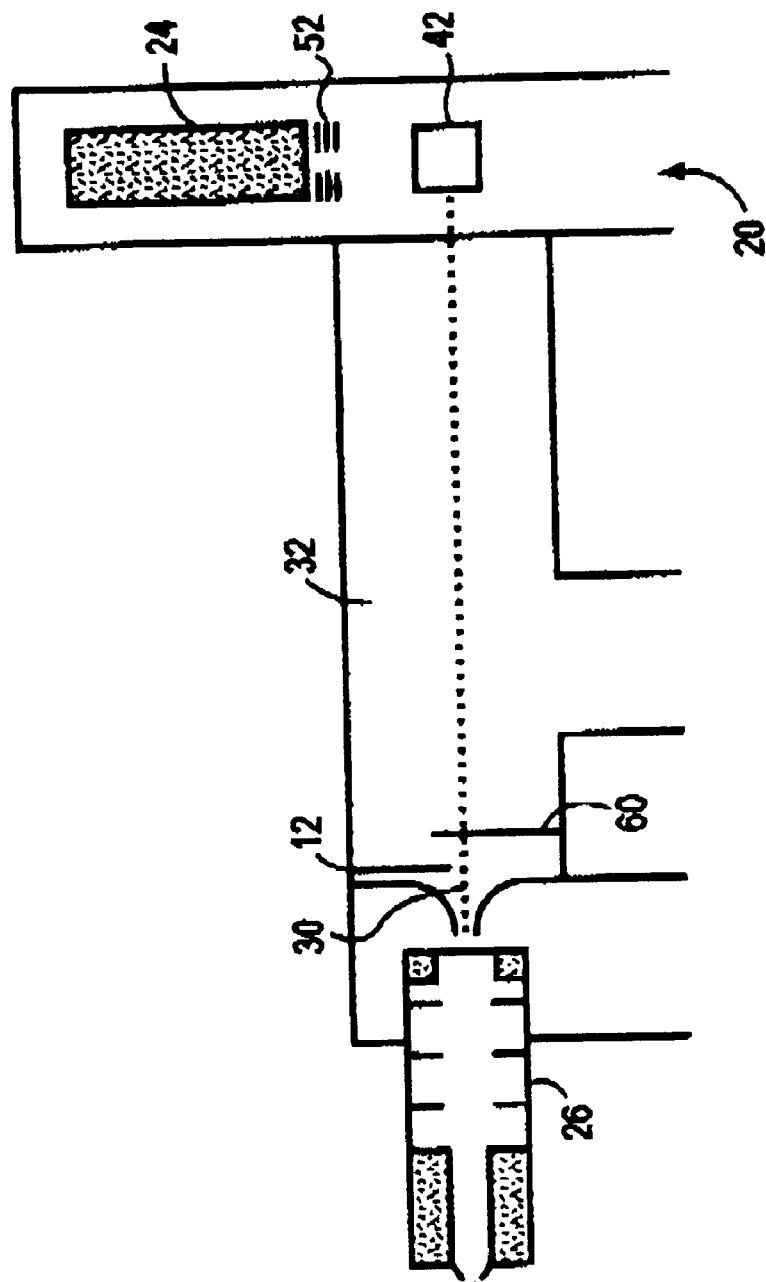
FIG. 3 is a diagram of a second embodiment of a particle analyzer incorporating the invention.

In FIG. 3 we have depicted another embodiment of the invention in which the particles of different size are separated by time of flight. A beam chopper 60, disposed at the outlet of the beam focuser 26, alternately blocks and passes the beam 12, so that a succession of beam pulses are passed to the detector 22. In passing through the beam focuser 26, the beam particles undergo a velocity dispersion. Specifically, the velocities of the particles emerging from the focuser are inversely related to particle size, that is, the smaller particles have higher velocities than the larger particles. Accordingly, as each beam pulse travels to the detector 42, it spreads in the direction of travel, with the smaller particles arriving at the detector 20 before the larger particles.

The beam chopper 60 can, for example, be a tuning fork magnetically driven at its resonance frequency, with a slit cut into one of its tines; or can be a rotating slotted disk. The chopper period, flight path and sampling duty cycle (fractional period of time the particle beam is un-blocked) are optimized for the range of particles which are to be sized. For example, in one embodiment of the invention a flight path of 50 cm to the detector 22, a beam chopping period of 10 milliseconds and a sampling duty cycle of 2% allows particles in the size range of 0.1 to 10 $\mu$m diameter to be sized into approximately 40 discrete size bins. Increasing the chopper duty cycle increases particle throughput (and hence signal levels) but decreases the resolution of the particle size measurement.

The particle size resolution obtained with deflection separation, as depicted in FIG. 1, will generally be greater than the resolution obtained with time-of-flight separation. However the analyzer in FIG. 3 has a simpler construction. It is therefore less expensive to build and further, is easier to maintain and consumes less electrical power. It is therefore better suited for large scale deployment in unattended sites. In any case both embodiments of the invention provide a function not previously available, namely, the analysis of atmosphere-entrained particles in a small easily deployable unit that does not require a high degree of expertise for its operation.

What is claimed is:

1. An analyzer for analyzing the particulate content of an atmosphere, said apparatus comprising
    A. means for extracting a sample of said atmosphere and forming a beam of the particles contained therein;
    B. means for sorting the particles in the beam according to particle size; and
    C. means for detecting and analyzing the volatile and semi-volatile components of the sorted particles on a per particle basis, thereby to provide a measure of the numbers and constituents of the particles of the various sizes.

2. The analyzer defined in claim 1 including
    A. A hollow tapered projection axially aligned with the beam and positioned upstream from the sorting means, the projection having an upstream narrow aperture end and a wide downstream end, and
    B. including means forming an aperture in said upstream end, said beam passing through said aperture, whereby gas molecules surrounding the particles in the beam are skimmed from the beam particles.

3. The analyzer defined in claim 2 in which the projection has a hyperbolic taper.

4. The analyzer defined in claim 1 in which said sorting means comprises:
    A. means for charging the particles in the beam;
    B. means for applying a variable electric field to the charged particles thereby to deflect them from the beam axis;
    C. means forming an aperture off the axis of the beam, whereby particles of a selected size pass through the aperture; and
    D. means for varying said electric field thereby to pass particles of a succession of sizes through the aperture.

5. The analyzer defined in claim 1 in which said detecting means comprises:

A. a molecular mass spectrometer;
B. means for vaporizing the volatile constituents of the particles;
C. means for charging the volatile constituents; and
D. means for directing the charged volatile constituents to the spectrometer.

6. The analyzer defined in claim 1
A. in which said beam-forming means forms a beam in which the velocity of the particles varies according to particle size; and
B. said sorting means comprises:
   1. a movable member disposed in the path of the particle beam;
   2. means forming an aperture in the member;
   3. means for moving said member so that said beam periodically passes through said aperture, thereby to form beam pulses that spread in the direction of beam travel, whereby the time of flight of the particles from the movable member to the detector depends on particle size.

7. The analyzer defined in claim 6 including means for correlating the output of the mass spectrometer with the timing of said beam pulses, thereby to provide a relationship between particle constituents and particle size.

* * * * *

UNITED STATES PATENT AND TRADEMARK OFFICE
CERTIFICATE OF CORRECTION

PATENT NO.    : 6,040,574
DATED         : March 21, 2000
INVENTOR(S)   : John T. Jayne et al.

It is certified that error appears in the above-identified patent and that said Letters Patent is hereby corrected as shown below:

<u>Column 1,</u>
Line 1, insert:
-- This invention was made with Government support under grant no. DMI-9705610 awarded by the National Science Foundation. The Government, has certain rights in this invention. --

Signed and Sealed this

Second Day of July, 2002

*Attest:*

JAMES E. ROGAN
*Attesting Officer*   *Director of the United States Patent and Trademark Office*